US012589058B2

(12) United States Patent
Cantero et al.

(10) Patent No.: US 12,589,058 B2
(45) Date of Patent: Mar. 31, 2026

(54) METHOD OF DISPERSING HYDROPHOBIC SUBSTANCES IN AQUEOUS CLEANSING SYSTEM

(71) Applicant: Renmatix, Inc., King of Prussia, PA (US)

(72) Inventors: Danilo Alberto Cantero, Wynnewood, PA (US); Jeremy Roland Austin, Malvern, PA (US); Konstantinos M. Lahanas, Paramus, NJ (US)

(73) Assignee: RENMATIX, INC., Wayne, PA (US)

( * ) Notice: Subject to any disclaimer, the term of this patent is extended or adjusted under 35 U.S.C. 154(b) by 0 days.

(21) Appl. No.: 18/385,805

(22) Filed: Oct. 31, 2023

(65) Prior Publication Data

US 2024/0082117 A1    Mar. 14, 2024

Related U.S. Application Data

(63) Continuation of application No. 17/346,402, filed on Jun. 14, 2021, now abandoned.

(60) Provisional application No. 63/038,706, filed on Jun. 12, 2020.

(51) Int. Cl.
| | |
|---|---|
| *A61K 8/06* | (2006.01) |
| *A61K 8/02* | (2006.01) |
| *A61K 8/73* | (2006.01) |
| *C11D 3/22* | (2006.01) |
| *C11D 17/00* | (2006.01) |

(52) U.S. Cl.
CPC .............. *A61K 8/06* (2013.01); *A61K 8/0241* (2013.01); *A61K 8/731* (2013.01); *C11D 3/222* (2013.01); *C11D 17/0017* (2013.01); *A61K 2800/412* (2013.01)

(58) Field of Classification Search
CPC ........ A61K 8/06; A61K 8/0241; A61K 8/731; A61K 2800/412; C11D 3/222; C11D 17/0017
See application file for complete search history.

(56) References Cited

U.S. PATENT DOCUMENTS

| | | | |
|---|---|---|---|
| 5,393,461 | A | 2/1995 | Fillipova |
| 6,534,071 | B1 | 3/2003 | Tournilhac et al. |
| 6,977,238 | B1 * | 12/2005 | Wetzel ...................... A61K 8/73 |
| | | | 510/156 |
| 9,260,551 | B2 | 2/2016 | Cathala et al. |
| 10,010,490 | B2 | 7/2018 | Hayashi et al. |
| 10,092,885 | B2 | 10/2018 | Bormashenko |
| 10,131,715 | B2 | 11/2018 | Hepworth et al. |
| 2012/0244134 | A1 | 9/2012 | Chen et al. |
| 2013/0122071 | A1 | 5/2013 | Cathala et al. |
| 2014/0073706 | A1 | 3/2014 | Capron et al. |
| 2015/0110841 | A1 | 4/2015 | Weichers et al. |
| 2015/0166836 | A1 | 6/2015 | Liu et al. |
| 2016/0303004 | A1 | 10/2016 | Ma |
| 2016/0333525 | A1 | 11/2016 | Welsch et al. |
| 2017/0000903 | A1 | 1/2017 | Olkowski et al. |
| 2017/0267827 | A1 | 9/2017 | Rowan et al. |
| 2017/0319458 | A1 | 11/2017 | Matsufuji et al. |
| 2019/0008749 | A1 * | 1/2019 | Harris ................... A61Q 17/04 |
| 2019/0037837 | A1 | 2/2019 | Wurm et al. |
| 2021/0386631 | A1 | 12/2021 | Cantero et al. |

FOREIGN PATENT DOCUMENTS

| | | |
|---|---|---|
| CA | 3174134 | 6/2020 |
| CN | 102553470 | 7/2012 |
| CN | 102309943 | 11/2012 |
| CN | 105395423 | 3/2016 |
| CN | 105411880 | 3/2016 |
| CN | 105994697 | 10/2016 |
| CN | 106750375 | 5/2017 |
| CN | 107141387 | 9/2017 |
| CN | 110563964 | 12/2019 |
| JP | 2000026229 | 1/2000 |
| JP | 2008260736 | 10/2008 |
| JP | 6216574 | 3/2015 |
| WO | WO0016889 | 3/2000 |
| WO | WO09027538 | 3/2009 |
| WO | WO10058148 | 5/2010 |
| WO | WO16124522 | 11/2016 |
| WO | WO19008145 | 1/2019 |
| WO | WO19008147 | 1/2019 |
| WO | PCT/US2020/037621 | 6/2020 |
| WO | WO2021/251987 | 12/2021 |

OTHER PUBLICATIONS

U.S. Appl. No. 63/038,706, filed Jun. 12, 2020, Cantero, et al. (Renmatix, Inc.).

U.S. Appl. No. 17/346,402, filed Jun. 14, 2021, Cantero, et al. (Renmatix, Inc.).

Duffus, et al. (2016), "A comparative study on the capacity of a range of food-grade particles to form stable O/W and W/O Pickering emulsions," J Colloid Interface Sci.; 473:9-21.

Kargar, et al. (2012), "Investigation into the potential ability of Pickering emulsions (food-grade particles) to enhance the oxidative stability of oil-in-water emulsions." J Colloid Interface Sci.; 366(1):209-215.

* cited by examiner

*Primary Examiner* — Doan T Phan

(74) *Attorney, Agent, or Firm* — Ballard Spahr LLP

(57) ABSTRACT

This disclosure relates to a method for making a dispersion, comprising preparing an aqueous phase comprising water and a surfactant; combining a hydrophobic substance and a plurality of particles comprising cellulose to form a concentrate; and mixing the aqueous phase and concentrate to provide a dispersion. This abstract is intended as a scanning tool for purposes of searching in the particular art and is not intended to be limiting of the present disclosure.

18 Claims, 1 Drawing Sheet

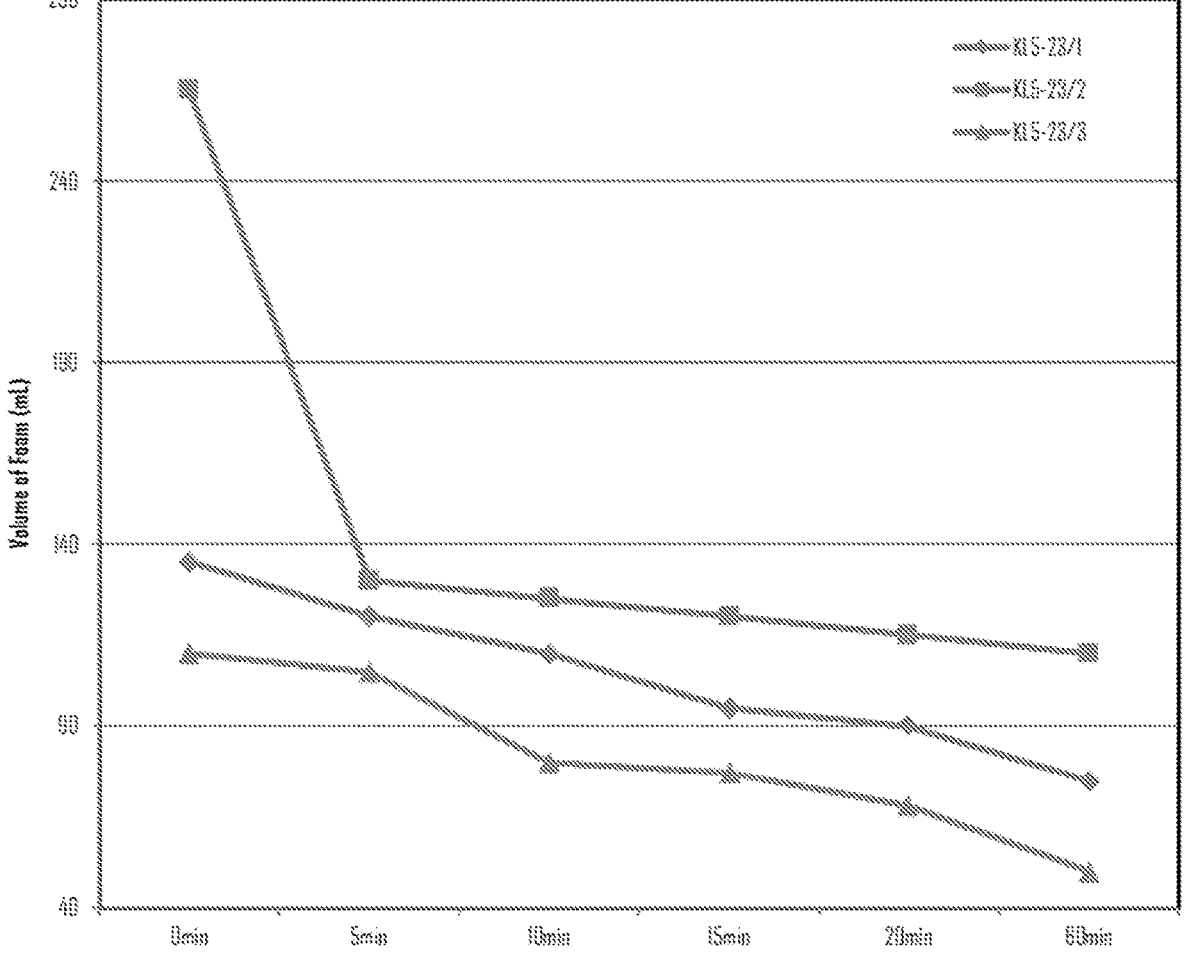

METHOD OF DISPERSING HYDROPHOBIC SUBSTANCES IN AQUEOUS CLEANSING SYSTEM

CROSS-REFERENCE TO RELATED APPLICATIONS

This application is a Continuation of U.S. application Ser. No. 17/346,402, filed Jun. 14, 2021, which claims priority to U.S. Provisional Application No. 63/038,706, filed Jun. 12, 2020, the contents of which are incorporated herein by reference in their entireties.

BACKGROUND

A common problem encountered when incorporating hydrophobic substances into a dispersion such as an emulsion is inadequate physical stability. Droplets or particles of the hydrophobic substance tend to flocculate, agglomerate, and settle-out from the dispersion or emulsion. As a result, a need exists for improved methods for incorporating hydrophobic substances into dispersions, particularly dispersions comprising an aqueous cleansing system. These needs and others are met by the following disclosure.

SUMMARY

In one aspect, this disclosure relates to a method for making a dispersion, comprising preparing an aqueous phase comprising water and a surfactant; combining a hydrophobic substance and a plurality of particles comprising cellulose to form a concentrate; and mixing the aqueous phase and concentrate to provide the dispersion. The cellulose particles can have a mean particle size of from about 0.1 to about 100 microns, an aspect ratio of from about 1 to about 1.5, and a non-spherical shape.

According to one aspect, the weight % of the hydrophobic substance in the concentrate prior to combining the concentrate with the aqueous phase can be from about 40 to about 60. According to a further aspect, water can be added to the concentrate prior to combining the concentrate with the aqueous phase. The concentrate, for example, can comprise from about 20 to about 50 weight % water prior to mixing the concentrate with the aqueous phase. According to a further aspect, the weight % of the cellulose particles in the concentrate prior to combining the concentrate with the aqueous phase can be from about 0.05 to about 30 weight %.

Also disclosed is a dispersion prepared by the method. Various commercial products can comprise the dispersion, including without limitation powders, grains, pastes, concentrates, foams, cleaning products, personal care or beauty products such as shampoo and body wash, and home and industrial cleaning products and polishes, among other products.

Still other objects and advantages of the present disclosure will become readily apparent by those skilled in the art from the following detailed description, which is shown and described by reference to preferred aspects, simply by way of illustration of the best mode. As will be realized, the disclosure is capable of other and different aspects, and its several details are capable of modifications in various respects, without departing from the disclosure. Accordingly, the description is to be regarded as illustrative in nature and not as restrictive.

BRIEF DESCRIPTION OF THE DRAWINGS

The accompanying drawings, which are incorporated in and constitute a part of this specification and together with the description, serve to explain the principles of the disclosure.

FIG. 1. is a plot of relative changes over the course of time for cleansing compositions prepared from the following dispersions: KL5-23/1, KL5-23/2, and KL5-23/3.

DETAILED DESCRIPTION

The present invention can be understood more readily by reference to the following detailed description of the invention and the Examples included therein.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

While aspects of this disclosure can be described and claimed in a particular statutory class, such as the system statutory class, this is for convenience only and one of skill in the art will understand that each aspect of this disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or description that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that this application is not entitled to antedate such publication by virtue of prior invention. Further, stated publication dates may be different from actual publication dates, which can require independent confirmation.

A. DEFINITIONS

Listed below are definitions of various terms. These definitions apply to the terms as they are used throughout this specification, unless otherwise limited in specific instances, either individually or as part of a larger group.

As used in the specification and in the claims, the term "comprising" can include the aspects "consisting of" and "consisting essentially of".

As used in the specification and claims, the singular forms "a," "an," and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

"Optional" or "optionally" means that the subsequently described event or circumstance may or may not occur, and that the description includes instances where said event or circumstance occurs and instances where it does not.

As used herein, the term "by weight," when used in conjunction with a component, unless specially stated to the contrary is based on the total weight of the formulation or composition in which the component is included. For example, if a particular element or component in a composition or article is said to have 8% by weight, it is understood that this percentage is in relation to a total compositional percentage of 100%.

A weight percent of a component, or weight %, or wt %, unless specifically stated to the contrary, is based on the total weight of the formulation or composition in which the component is included.

References in the specification and concluding claims to parts by weight of a particular element or component in a composition or article, denotes the weight relationship between the element or component and any other elements or components in the composition or article for which a part by weight is expressed. Thus, in a composition or a selected portion of a composition containing 2 parts by weight of component X and 5 parts by weight component Y, X and Y are present at a weight ratio of 2:5, and are present in such ratio regardless of whether additional components are contained in the composition.

As used herein, the term "substantially," in, for example, the context "substantially free of" refers to a composition having less than about 10% by weight, e.g., less than about 5%, less than about 1%, less than about 0.5%, less than about 0.1%, less than about 0.05%, or less than about 0.01% by weight of the stated material, based on the total weight of the composition.

It is further understood that the term "substantially," when used in reference to a composition, refers to at least about 60% by weight, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% by weight, based on the total weight of the composition, of a specified feature, component, or a combination of the components. It is further understood that if the composition comprises more than one component, the two or more components can be present in any ratio predetermined by one of ordinary skill in the art.

"Dispersion," as used herein, refers to a dispersion of hydrophobic substance(s) in water, stabilized by the cellulose particles described herein. According to one aspect, the dispersion is a homogenous dispersion. The homogeneous dispersion can be a visually-homogeneous dispersion and/or a dispersion having a constant concentration of the hydrophobic substance(s) and/or cellulose particles, i.e., the concentration of a substance in one region of the dispersion can be about the same or the same as the concentration of the same substance in a different region of the dispersion. According to a further aspect, the dispersion, e.g., a homogeneous dispersion, can be an emulsion or a stable emulsion.

"Surfactant," as used herein, is a compound that contains a lipophilic segment and a hydrophilic segment, which when added to water or solvents, reduces the surface tension of the system. Non-limiting examples include a sulfate, sulfonate, isethionate, carboxylate, sarcosinate, amino acid-based surfactant, non-ionic surfactant, soap, and sulfoacetate.

"Hydrophobic substance," as used herein, refers to a substance that is substantially insoluble in water. Non-limiting examples include a natural or synthetic oil, silicon, fat, emollient, and a triester of glycerol. The term also includes a hydrophobic substance having solubility in water below about 0.1 mg/mL.

"Emollient," as used herein, refers to a greasy, fatty, waxy, or oily substance that is capable of softening or soothing the skin, including without limitation liquids, semi solids, and solids. The emollient can be an unctuous emollient, i.e., it can have a greasy or soapy feel. Examples of suitable emollients include without limitation fatty alcohols, esters and triglycerides. Other suitable emollients are described in Sagarin, Cosmetics, Science and Technology, 2nd Edition, Vol. 1, pp. 32-43 (1972), which is incorporated herein by reference for its teachings of emollients.

"Volatile organic solvent," as used herein, means any compound of carbon that vaporizes or evaporates easily at room temperature, e.g., a compound having a boiling point lower than about 100° C.

As used herein, the term "degree of polymerization" (DP) is defined as the number of monomeric units in a macro-molecule, polymer, or oligomer. For example, the number-average degree of polymerization can be calculated with the following formula:

$$DP_n = X_n = \frac{M_n}{M_0}$$

where $M_n$ is the number-average molecular weight and $M_0$ is the molecular weight of the monomer unit. For cellulose, the monomer unit is the anhydroglucose unit (glucose minus the equivalent of one water molecule, 162 g/mol).

"Z-average molecular weight," or "$M_z$," means a value calculated by the following equation:

$$Mz = \frac{\Sigma M_i^2 c_i}{\Sigma M_i c_i}$$

where $M_z$ is the Z-average molecular weight, $M_i$ is the molecular weight of fraction i, and $c_i$ is the concentration of fraction i.

"Aspect ratio" refers to the ratio of the largest dimension of a particle to the smallest dimension (e.g., length/diameter for a cylinder; length/thickness for a plate; or longest axis/shortest axis for an ellipsoid).

"Hydrophile-lipophile balance (HLB) number" refers to the degree to which a surfactant is hydrophilic or lipophilic. The number can be calculated using Griffin's method, where $HLB=20 \times M_h/M$, where $M_h$ is the molecular mass of the hydrophilic portion of the molecule, and M is the molecular mass of the entire molecule. The equation yields a result on a scale of 0 to 20. An HLB value of 0 corresponds to a completely lipophilic/hydrophobic molecule, and a value of 20 corresponds to a completely hydrophilic/lipophobic mol-ecule.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

B. METHODS FOR MAKING THE DISPERSIONS

In one aspect, the method for making the dispersion comprises (a) preparing an aqueous phase comprising water and a surfactant; and (b) combining a hydrophobic substance and a plurality of particles comprising cellulose to provide a concentrate. The plurality of particles comprising cellulose can have a mean particle size of from about 0.1 to about 100 microns, an aspect ratio of from about 1 to about 1.5, and a non-spherical shape. The aqueous phase comprising water and the surfactant can be mixed with the concentrate to provide the dispersion.

One advantage of the method is that, in some aspects, the aqueous phase, the concentrate, and the resultant dispersion can be substantially free of volatile organic solvent. For example, the aqueous phase, the concentrate, and the resultant dispersion can comprise less than about 10% by weight, e.g., less than about 5%, less than about 1%, less than about 0.5%, less than about 0.1%, less than about 0.05%, or less than about 0.01% by weight of volatile organic solvent, based on the total weight of the composition. In a further aspect, the aqueous phase, the concentrate, and the resultant dispersion can be free of volatile organic solvent. Similarly, the steps of the method for making the dispersion can be carried out in an environment that is substantially free of or free of volatile organic solvent.

According to one aspect, the aqueous phase, the concentrate, and the resultant dispersion can be substantially free or free of an organic solvent, whether volatile or not. For example, the aqueous phase, the concentrate, and the resultant dispersion can be substantially free or free of ethyl alcohol, methyl alcohol, isopropyl alcohol, chloromethane, dichloromethane, chloroform, carbon tetrachloride, methyl ethyl ketone, methyl isobutyl, ketone, ethyl acetate, perchlo-roethylene, acetone, and glycol ethers.

Another advantage of the method is that, in some aspects, the concentrate need not be contacted with a surfactant or wetting agent prior to mixing the concentrate with the aqueous phase. Thus, for example, prior to mixing the concentrate with the aqueous phase, the concentrate can be substantially free of or free of any of the following surfac-tants or wetting agents: sodium dodecyl benzene sulfonate, alkyl benzene sulfonate, sodium lauryl sulfate, sodium dioc-tyl sulfosuccinate, sodium-dilauryl phosphate, lanolin and lanolin derivatives, sodium monoglyceryl lauryl sulfate, sodium methyl oleoyl taurate, sodium octoxynol-2-ethane-sulfonate, sodium dioctyl sulfosuccinate, sodium octoxynol-2-ethane sulfonate, di-β-naphthylmethane disulfate, sulfated castor oil, sodium secondary alcohol sulfate, sodium alky-laryl sulfonate (AEROSOL OS), dialkylsulfosuccinate (AEROSOL MA), dioctyl ester of sodium sulfosuccinate (AEROSOL OT), sodium-2-ethylhexyl sulfate (TERGITOL 08), sodium-7-ethyl-2-methyl-undecyl-4-sulfate (TERGI-TOL 04), and sodium-3,9-diethyltridecyl-6-sulfate (TERGI-TOL 07).

A variety of substances can be added to the concentrate comprising the hydrophobic substance and the plurality of cellulose particles. According to one aspect, the hydrophobic substance and the plurality of particles can be combined with glycerin, a glycol, a hydroxy ester, or a combination thereof while forming the concentrate. In a further aspect, the hydrophobic substance and the plurality of particles can be combined with a preservative while forming the concen-trate.

According to one aspect, it can be preferable to prepare the aqueous phase separately from the concentrate. It has been discovered that a one-pot approach, wherein the aque-ous phase and the concentrate are formed simultaneously, does not result in a stable or homogeneous dispersion. For example, it was observed that a one-pot approach yields discrete separated phases. Without wishing to be bound by theory, it is believed that the surfactant may interfere with the ability of the cellulose particles and/or the hydrophobic substance to form a stable or homogeneous dispersion when the surfactant contacts the particles or hydrophobic sub-stance prior to the concentrate being formed. Thus, it can be desirable in some aspects to prepare the aqueous phase with the surfactant separately from the concentrate, and then combine the aqueous phase with the concentrate.

In some aspects, the dispersion can be a stable dispersion. In a further aspect, the dispersion can be a homogeneous dispersion, such as a visually-homogeneous dispersion. In a still further aspect, the dispersion can be a homogeneous dispersion having a constant concentration of the hydrophobic substance(s) and/or the cellulose particles, i.e., the concentration of the substance in one region of the dispersion is about the same or the same as the concentration of the same substance in a different region of the dispersion. In yet a further aspect, the dispersion can be an emulsion or a stable emulsion.

1. Surfactants

In some aspects, the aqueous phase comprises water and a surfactant. According to one aspect, the surfactant has a hydrophile-lipophile balance (HLB) number of greater than 10. In a further aspect, the surfactant is a sulfate, sulfonate, isethionate, carboxylate, sarcosinate, amino acid-based surfactant, non-ionic surfactant, soap, sulfoacetate, or a combination thereof.

In a still further aspect, the surfactant is sodium lauryl sulfate, sodium lauryl ether sulfate, a sodium olefin sulfonate comprising from 14 to 16 carbons (e.g., Sodium C14-16 Olefin Sulfonate known as NANSA™ LSS 38/U, available from Innospec), sodium lauroyl isethionate, sodium cocoyl isethionate (e.g., Pureact I-85EC, available from Innospec), sodium lauroyl methyl isethionate (e.g., ISELUX™ LQ-CLR-SB, available from Innospec), sodium laureth sulfate (e.g., Sulfochem ES-2PK, available from Lubrizol), disodium lauroamphodiacetate, disodium cocoamphodiacetate, disodium cocoamphodipropionate, sodium lauroyl sarcosinate, sodium cocoyl sarcosinate, sodium lauroyl lactylate, disodium coco-glucoside citrate, disodium cocoyl glutamate, sodium cocoyl glycinate, cocamidopropyl betaine (e.g., CHEMBETAINE™ CGF, available from Lubrizol), cocamide MEA (e.g., Protamid CME, available from Protameen Chemicals), polysorbate 20, decyl glucoside, sodium stearate, potassium stearate, sodium oleate, potassium oleate, sodium lauryl sulfoacetate, or a combination thereof, including for example a combination of decyl glycoside, sodium lauroyl lactylate, and disodium coco-glucoside citrate (e.g., Ritafactant 138 ANEC, available from Rita Corp.).

The surfactant can be present in the aqueous phase in varying amounts. According to one aspect, the weight % of the surfactant in the aqueous phase, prior to mixing the aqueous phase with the hydrophobic phase (concentrate), ranges from about 10% by weight to about 60% by weight. In a further aspect, the weight % of the surfactant in the aqueous phase, prior to mixing the aqueous phase with the hydrophobic phase, ranges from about 10% by weight to about 50% by weight. In a still further aspect, the weight % of the surfactant in the aqueous phase, prior to mixing the aqueous phase with the hydrophobic phase, ranges from about 10% by weight to about 40% by weight. In yet a further aspect, the weight % of the surfactant in the aqueous phase, prior to mixing the aqueous phase with the hydrophobic phase, ranges from about 20% by weight to about 40% by weight. In another aspect, the weight % of the surfactant in the aqueous phase, prior to mixing the aqueous phase with the hydrophobic phase, ranges from about 30% by weight to about 50% by weight, e.g., from about 30% by weight to about 40% by weight.

In some aspects, the ratio of the surfactant to water in the aqueous phase, prior to mixing the aqueous phase with the hydrophobic phase, ranges from about 0.1 to about 2. In a further aspect, the ratio of the surfactant to water in the aqueous phase, prior to mixing the aqueous phase with the hydrophobic phase, ranges from about 0.5 to about 1.5. In a still further aspect, the ratio of the surfactant to water in the aqueous phase, prior to mixing the aqueous phase with the hydrophobic phase, ranges from about 0.7 to about 1.5.

2. Hydrophobic Substances

The method allows for the introduction of a variety of hydrophobic substances into the dispersion. According to one aspect, the hydrophobic substance is synthetic. In a further aspect, the hydrophobic substance is derived from a plant or other organic material. In a still further aspect, the hydrophobic substance comprises an oil, a silicone, a fat, an emollient, a triester of glycerol, or a combination thereof.

According to one aspect, the hydrophobic substance comprises isopropyl palmitate, octyl hydroxy stearate, octyldodecyl steroyl stearate, shea butter, cocoa butter, petrolatum, tea tree oil, jojoba oil, sunflower oil, borage oil, mineral oil, squalene, or a combination thereof.

Other non-limiting examples of suitable hydrophobic substances include *Simmondsia chinesis* (Jojoba) seed oil, *Helianthus annuus* (sunflower) seed oil, *Amaranthus caudatus* seed extract, diisostearyl malate, *Rosmarinus pfficinahs* (Rosemary) leaf extract, borage oil, *Oenothera biennis* (evening primrose) oil, or a combination thereof, including for example a combination of *Helianthus annuus* (sunflower) seed oil, *Amaranthus caudatus* seed extract, diisostearyl malate, and *Rosmarinus pfficinalis* (Rosemary) leaf extract (AMA Oil, available from Centerchem).

In some aspects, the hydrophobic substance can be a natural or non-natural fragrance. Non-limiting examples include lemon oil, lavender oil, peppermint oil, amber oil, grapefruit oil, clove oil, orange clove oil, coconut oil, almond oil, honeydew oil, rosemary oil, pomegranate oil, anise oil, laurel oil, bergamot essence, bitter almond, camphor, cedar leaf oil, cinnamon oil, citronella oil, eucalyptus oil, mustard oil, pine oil, pine needle oil, spearmint oil, sassafras oil, thyme oil, wintergreen oil, and the like.

The amount of hydrophobic substance in the concentrate (prior to mixing the concentrate with the aqueous phase) can vary within wide limits. According to one aspect, the weight % of the hydrophobic substance in the concentrate prior to mixing the concentrate with the aqueous phase can be at least about 10. In a further aspect, the weight % of the hydrophobic substance in the concentrate prior to mixing the concentrate with the aqueous phase can be from about 40 to about 60. In a still further aspect, the weight % of the hydrophobic substance in the concentrate prior to mixing the concentrate with the aqueous phase can be from about 50 to about 60.

The ratio of the hydrophobic substance to the cellulose particles in the concentrate, prior to mixing the concentrate with the aqueous phase, can also vary. In some aspects, the ratio of the hydrophobic substance to the cellulose particles in the concentrate, prior to mixing the concentrate with the aqueous phase, is from about 2:1 to about 10:1. In a further aspect, the ratio of the hydrophobic substance to the cellulose particles in the concentrate, prior to mixing the concentrate with the aqueous phase, is from about 6:1 to about 10:1. In a still further aspect, the ratio of the hydrophobic substance to the cellulose particles in the concentrate, prior to mixing the concentrate with the aqueous phase, is about 8:1. In another aspect, the ratio of the hydrophobic substance to the cellulose particles in the concentrate, prior to mixing the concentrate with the aqueous phase, is about 2:1.

In some aspects, once combined with the aqueous phase, the amount of hydrophobic substance in the dispersion can be at least about 5% by weight. In a further aspect, the amount of hydrophobic substance in the dispersion can be at least about 10% by weight. In a further aspect, the weight % of the hydrophobic substance in the dispersion is from about 5 to about 50. In another aspect, the weight % of the hydrophobic substance in the dispersion is from about 10 to about 50. In a still further aspect, the weight % of the hydrophobic substance in the dispersion is from about 10 to about 20. According to another aspect, the weight % of the hydrophobic substance in the dispersion is from about 10 to about 15, e.g., about 10.

According to one aspect, water can be added to the concentrate comprising the hydrophobic substance and the cellulose particles prior to mixing to the concentrate with the aqueous phase. The weight % of the water in the concentrate, prior to mixing with the aqueous phase, can in some aspects be from about 10 to about 50. In a further aspect, the weight % of the water in the concentrate, prior to mixing with the aqueous phase, can be from about 20 to about 50, e.g., from about 25 to about 50, from about 20 to about 40, or from about 20 to about 30.

When water is added to the concentrate prior to mixing the concentrate with the aqueous phase, the ratio of the hydrophobic substance to water in the concentrate (prior to mixing with the aqueous phase) can be from about 1:1 to about 2:1. In a further aspect, the ratio of the hydrophobic substance to water in the concentrate (prior to mixing with the aqueous phase) can be from about 1:1 to about 1.8:1. For example, the ratio of the hydrophobic substance to water in the concentrate (prior to mixing with the aqueous phase) can be about 1.3:1 or about 2:1.

3. Particles Comprising Cellulose

In one aspect, the hydrophobic substance can be combined with a plurality of particles comprising cellulose. The plurality of cellulose particles can function to stabilize the dispersions and allow for the integration of hydrophobic substances in the dispersions. In some aspects, the plurality of particles comprising cellulose allow for the delivery of high contents of hydrophobic substances in a surfactant-containing system, while maintaining desired foaming characteristics of a cleansing product.

According to one aspect, the weight % of the cellulose particles in the concentrate prior to mixing the concentrate with the aqueous phase can be at least about 0.05%. In some aspects, the weight % of the cellulose particles in the concentrate prior to mixing the concentrate with the aqueous phase can be at least about 0.5%. In a further aspect, the weight % of the cellulose particles in the concentrate prior to mixing the concentrate with the aqueous phase can be from about 0.05% to about 40%. In a further aspect, the weight % of the cellulose particles in the concentrate prior to mixing the concentrate with the aqueous phase can be from about 0.05% to about 30%. In a still further aspect, the weight % of the cellulose particles in the concentrate prior to mixing the concentrate with the aqueous phase can be from about 10% to about 30%. In a still further aspect, the weight % of the cellulose particles in the concentrate prior to mixing the concentrate with the aqueous phase can be from about 20% to about 30%, e.g., about 23% to about 25%. In another aspect, the weight % of the cellulose particles in the concentrate prior to mixing the concentrate with the aqueous phase can be from about 0.05% to about 10% or 0.5% to about 10%.

In some aspects, the cellulose particles can be provided as a slurry. In one aspect, the cellulose particles can be provided as a slurry comprising at least about 10% by weight cellulose particles. In another aspect, the cellulose particles can be provided as a slurry comprising at least about 20% by weight cellulose particles. In other aspects, the cellulose particles can be provided as a slurry comprising at least about 25% by weight cellulose particles. In a further aspect, the cellulose particles can be provided as a slurry comprising at from about 25% by weight to about 90% by weight cellulose particles, e.g., from about 25% to about 80%, from about 25% to about 70%, from about 25% to about 60%, from about 25% to about 50%, from about 25% to about 40%. The balance of the slurry can be any suitable ingredient, such as water, glycerin, acer rubrum extract, or a combination thereof. A specific non-limiting example of a suitable slurry is CELLTICE™ WM (available from Renmatix), which comprises 25% by weight cellulose particles.

a. Composition of the Cellulose Particles

In some aspects, the particles comprise cellulose in an amount ranging from about 40 weight % to about 100 weight %, based on the total dry weight of the particles. Thus, for example, the particles can comprise about 40, 42, 45, 46, 48, 50, 52, 54, 56, 58, 60, 62, 64, 66, 68, 70, 72, 72, 76, 78, 80, 82, 84, 86, 88, 90, 92, 94, 95, 96, 97, 98, 99, or 100 weight % cellulose, based on the total dry weight of the particles. In one aspect, the particles comprise cellulose in an amount ranging from about 70 weight % to about 99 weight %, based on the total dry weight of the particles. In a further aspect, the particles comprise cellulose in an amount ranging from about 80 weight % to about 98 weight %, based on the total dry weight of the particles.

In some aspects, a portion of the cellulose in the particles can be type-I cellulose. The amount of type-I cellulose in the particles can vary. For example, the particles can comprise type-I cellulose in an amount ranging from about 1 weight % to about 99 weight %, based on the total amount of cellulose in the particles. For example, the particles can comprise about 1, 5, 10, 15, 20, 25, 30, 35, 40, 45, 50, 55, 60, 65, 70, 75, 80, 85, 90, 95, or 99 weight % type-I cellulose, based on the total amount of cellulose in the particles.

Type-I cellulose can be converted to a stable crystalline form of cellulose known as a type-II cellulose. The conversion of type-I cellulose to type-II cellulose can be achieved by different routes, for example by mercerization (alkali treatment), regeneration (solubilization followed by recrystallization), subcritical and supercritical water, ball milling of cellulose in presence of water, and the like. The conversion can be irreversible, suggesting that type-II cellulose can be more stable than type-I cellulose.

In some aspects, at least a portion of the cellulose in the particles can be type-II cellulose. The amount of type-II cellulose in the particles can vary. For example, the particles can comprise type-II cellulose in an amount ranging from about 1 weight % to about 100 weight %, based on the total amount of cellulose in the particles. In a further aspect, the particles can comprise type-II cellulose in an amount ranging from about 5 weight % to about 95 weight %, based on the total amount of cellulose in the particles. In another aspect, the particles can comprise type-II cellulose in an amount ranging from about 10 weight % to about 80 weight %, based on the total amount of cellulose in the particles. In a still further aspect, the particles can comprise type-II cellulose in an amount ranging from about 20 weight % to about 70 weight %, based on the total amount of cellulose in the particles. In yet a further aspect, the particles can comprise type-II cellulose in an amount ranging from about 30 weight % to about 50 weight %, based on the total amount of cellulose in the particles. For example, the particles can comprise about 1, 5, 10, 15, 20, 25, 30, 35, 40, 45, 50, 55, 60, 65, 70, 75, 80, 85, 90, 95, or 100 weight % type-II cellulose, based on the total amount of cellulose in the particles. In some aspects, the particles comprising cellulose can comprise type-I and type-II cellulose, for example in any of the amounts listed above.

In one aspect, the cellulose particles can comprise type-I and type-II cellulose and can further comprise amorphous cellulose. The ratio of amorphous cellulose to the total amount of type-I and type-II cellulose, on a dry weight basis, can be about 0.5:9.5, 1:9, 1.5:9.5, 2:8, 2.5:7.5, 3:7, 3.5:6.5, 4:6, 4.5:5.5, 5:5, 5.5:4.5, 6:4, 6.5:3.5, 7:3, 7.5:2.5, 8:2, 8.5:1.5, 9:1, or 9.5:0.5. Relative amounts of type-I cellulose, type-II cellulose, and amorphous cellulose can be measured using solid-state $^{13}C$ CP-MAS NMR spectroscopy or x-ray diffraction (XRD). In some aspects, the cellulose particles comprise, consist of, or consist essentially of cellulose having a type-II structure, either alone or in combination with a type-I structure, an amorphous structure, or both. In one aspect, the ratio of type-I cellulose to type-II cellulose in the cellulose particles, on a dry weight basis, is about 0.5:9.5, 1:9, 1.5:9.5, 2:8, 2.5:7.5, 3:7, 3.5:6.5, 4:6, 4.5:5.5, 5:5, 5.5:4.5, 6:4, 6.5:3.5, 7:3, 7.5:2.5, 8:2, 8.5:1.5, 9:1, or 9.5:0.5.

According to one aspect, the particles can comprise other types of the cellulose. For example, the particles can comprise type-III cellulose and/or type-IV cellulose. Type-III and type-IV cellulose can be produced by various chemical treatments, such as treatment with liquid ammonia or certain amides such as ethylene diamine, or high temperature treatment in glycerol.

In some aspects, the cellulose particles can comprise lignin in an amount ranging up to about 80 weight %, based on the dry weight of the particles. According to one aspect, the weight % of lignin in the cellulose particles can be from about 1 to about 30. In a further aspect, the weight % of lignin in the cellulose particles can be from about 2 to about 20. Thus, for example, the cellulose particles can comprise 1, 2, 3, 4, 5, 6, 7, 8, 9, 10, 11, 12, 3, 14, 15, 6, 17, 18, 19, 20, 21, 22, 23, 24, 25, 26, 27, 28, 29, or 30 weight % lignin, based on the total dry weight of the particles. According to one aspect, at least a portion of the cellulose in the particles is type-II cellulose, and the particles further comprise lignin.

According to one aspect, the cellulose particles can be suitable for application to the skin or hair of a subject such as a human. Thus, for example, the cellulose particles can be substantially free of hazardous impurities and/or otherwise in compliance with regulations of the U.S. Food and Drug Administration (FDA) or other government agencies throughout the world. In some aspects, the cellulose particles comprise less than about 10 ppm of toxic metals, e.g., the group of transition metals, some metalloids, lanthanides, actinides, including without limitation lead, cadmium, vanadium, nickel, cobalt, mercury, chromium, arsenic, selenium, copper, manganese, iron, zinc, beryllium, and aluminum. In a further aspect, the cellulose particles can comprise less than about 5 ppm of toxic metals, e.g., from about 0.05 ppm to about 5 ppm, or from about 0.2 ppm to about 5 ppm.

a. Crystallinity and Molecular Weight Characteristics of the Cellulose Particles In various aspects, the particles comprising cellulose can have a number of crystalline structures. Natural cellulose, also known as a type-I cellulose, can comprise $I_\alpha$ and $I_\beta$ crystalline structures. The amount of $I_\alpha$ and $I_\beta$ crystalline structures can depend on the type of the natural cellulose. For example, cellulose produced by bacteria and algae can be enriched in $I_\alpha$ crystalline structures, while cellulose derived from plants can comprise mainly $I_\beta$ crystalline structures.

The crystalline phases of the cellulose in the particles can be analyzed using x-ray diffraction (XRD). The XRD pattern of a crystalline solid reflects the crystal structure. Using Cu $K_\alpha$ radiation, the XRD spectrum of type-I cellulose show two peaks at 2θ: a primary peak around 22.5° and a secondary peak around 15.5°. The XRD spectrum of type-II cellulose shows a primary peak at 2θ around 19.9° and a secondary peak around 12.1°.

In one aspect, the cellulose particles have a crystallinity determined by XRD of 60% or more. In a further aspect, the cellulose particles have a crystallinity determined by XRD of 70% or more. For example, the cellulose particles can have a crystallinity determined by XRD of about 60%, about 70%, about 72%, about 74%, about 76%, about 78%, about 80%, about 82%, about 84%, about 86%, about 88%, about 90%, about 92%, about 94%, about 96%, about 98%, about 99%, or about 100%.

The cellulose in the particles can have a variety of molecular weights. In some aspects, the cellulose particles can comprise cellulose having a weight-average molecular weight ($M_w$ in units of g/mol) of from about 2000 g/mol to about 180000 g/mol. For example, the cellulose particles can comprise cellulose having an $M_w$ (in units of g/mol) of about 2200, 2400, 2600, 2800, 3000, 3200, 3400, 3500, 3600, 3800, 4000, 4200, 4400, 4500, 4600, 4800, 5000, 5200, 5400, 5500, 5600, 5800, 6000, 6200, 6400, 6500, 6600, 6800, 7000, 7200, 7400, 7500, 7600, 7800, 8000, 8500, 9000, 9500, 10000, 10500, 11000, 11500, 12000, 12500, 13000, 13500, 14000, 14500, 15000, 15500, 16000, 16500, 17000, 17500, or 18000. In some aspects, the $M_w$ of the cellulose in the particles can be at least about 4000 g/mol, about 12000 g/mol to about 15500 g/mol, about 6000 g/mol to about 12000 g/mol, about 2200 g/mol to about 9500 g/mol, or less than about 13000 g/mol, as determined on a sample of the cellulose particles that has been prepared for gel-permeation chromatography (GPC) analysis.

The number-average molecular weight ($M_n$) of the cellulose in the particles can also vary. In some aspects, the cellulose in the particles can have an $M_n$ of from about 2000 g/mol to about 8000 g/mol. For example, the cellulose in the particles can have an $M_n$ (in units of g/mol) of about 2000, 2500, 3000, 3500, 4000, 4500, 5000, 5500, 6000, 6500, 7000, 7500, or 8000. In some aspects, the $M_n$ of the cellulose in the particles can be at least about 2000 g/mol, about 3000 g/mol to about 5500 g/mol, about 3000 g/mol to about 8000 g/mol, or less than about 7000 g/mol, as determined on a sample of the cellulose particles that has been prepared for GPC analysis.

The Z-average molecular weight ($M_z$) of the cellulose in the particles can similarly vary. For example, the cellulose in the particles can have an $M_z$ of from about 5000 g/mol to about 40000 g/mol. In some aspects, the cellulose in the particles can have an $M_z$ (in units of g/mol) about 5000, 5500, 6000, 6500, 7000, 7500, 8000, 8500, 9000, 9500, 10000, 10500, 11000, 11500, 12000, 12500, 13000, 13500, 14000, 14500, 15000, 16000, 17000, 18000, 19000, 20000, 21000, 22000, 23000, 24000, 25000, 26000, 27000, 28000, 29000, 30000, or 40000.

The cellulose in the particles can have any suitable degree of polymerization (DP). According to one aspect, the cellulose in the particles can have a weight average degree of polymerization ($DP_w$) of from about 10 to about 150. Thus, for example, the $DP_w$ of the cellulose in the particles can be about 10, 12, 14, 15, 16, 18, 20, 22, 24, 25, 26, 28, 30, 32, 34, 35, 36, 38, 40, 42, 44, 45, 46, 48, 50, 55, 60, 65, 70, 75, 80, 85, 90, 95, 100,105, 110, 115, 120, 125, 130, 135, 140, 145, or 150. In some aspects, the DP can be at least about 16, about 20 to about 95, about 40 to about 80, or less than about 150, as determined on a sample of the cellulose particles that has been prepared for GPC analysis. $DP_w$ can be calculated from $M_w$, using the anhydroglucose molar weight of 162 g/mol.

The number average degree of polymerization ($DP_n$) can be similarly calculated from the $M_n$ of the cellulose in the particles. According to some aspects, the cellulose particles can comprise cellulose having a $DP_n$ of from about 15 to about 150. For example, the cellulose can have a $DP_n$ of about 15, 16, 18, 20, 22, 24, 25, 26, 28, 30, 32, 34, 35, 36, 38, 40, 42, 44, 45, 46, 48, 50, 55, 60, 65, 70, 75, 80, 85, 90, 95, 100,105, 110, 115, 120, 125, 130, 135, 140, 145, or 150. In a further aspect, the $DP_n$ of the cellulose can be at least about 16, about 20 to about 95, about 25 to about 40, or less than about 150, as determined on a sample of the cellulose particles that has been prepared for GPC analysis.

According to one aspect, molecular weights and degrees of polymerization of the cellulose in the particles can be compared to microcrystalline cellulose (MCC), preferably MCC from Acros Organics (having an average particle size of 90 microns, Product No. 382310010). Thus, in some aspects, the cellulose in the particles can have an $M_n$ that is from about 0.05 to about 0.7 times the $M_n$ of MCC available from Acros, or another comparable MCC. For example, the cellulose in the particles can have an $M_n$ that is 0.05, 0.1, 0.15, 0.2, 0.25, 0.3, 0.35, 0.4, 0.45, 0.5, 0.55, 0.6, 0.65, or 0.7 times the $M_n$ of MCC available from Acros. Similarly, the cellulose in the particles can have an $M_w$ that is from about 0.04 to about 0.5 times the $M_w$ of MCC available from Acros. For example, the cellulose in the particles can have an $M_w$ that is 0.04, 0.02, 0.04, 0.06, 0.08, 0.1, 0.12, 0.14, 0.16, 0.18, 0.2, 0.22, 0.24, 0.26, 0.28, 0.3, 0.32, 0.34, 0.36, 0.38, 0.4, 0.42, 0.44, 0.46, 0.48, or 0.5 times the $M_w$ of MCC available from Acros. Likewise, the cellulose in the particles can have an $M_z$ that is from about 0.01 to about 0.36 times the $M_z$ of MCC available from Acros, e.g., about 0.01, 0.02, 0.03, 0.04, 0.05, 0.06, 0.07, 0.08, 0.09, 0.1, 0.12, 0.14, 0.15, 0.16, 0.18, 0.2, 0.22, 0.24, 0.26, 0.28, 0.3, 0.32, 0.34, or 0.36 times the $M_z$ of MCC. In some aspects, the DP of the cellulose in the particles can be from about 0.04 to about 0.5 times the DP of MCC available from Acros, e.g., about 0.04, 0.02, 0.04, 0.06, 0.08, 0.1, 0.12, 0.14, 0.16, 0.18, 0.2, 0.22, 0.24, 0.26, 0.28, 0.3, 0.32, 0.34, 0.36, 0.38, 0.4, 0.42, 0.44, 0.46, 0.48, or 0.5 times the DP of MCC.

The cellulose in the particles can have any suitable polydispersity index (PDI), also known simply as dispersity (Ð). PDI can be calculated using the equation $Ð_M=M_w/M_n$, or can be calculated according to DP, where $Ð_{DP}=DP_w/DP_n$. In some aspects, the cellulose in the particles can have a PDI of from about 1.0 to about 2.8, e.g., 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, or 2.8.

Molecular weights, degrees of polymerization, and values calculated therefrom such as PDI can be determined according to following method for preparing and solubilizing the cellulose in the particles for GPC analysis. The method is adapted from Dupont, Polymer, "Cellulose in lithium chloride/N,N-dimethylacetamide, optimization of a dissolution method using paper substrates and stability of the solutions," Vol. 44, (2003), 4117-4126, which is incorporated herein by reference in its entirety. The method involves several sequential steps: (i) swelling the particles comprising cellulose twice in deionized (DI) water for 1 hour each time while stirring at room temperature (followed by filtering and re-suspending solids in fresh DI water after each swelling), (ii) activating the resulting solids twice in methanol for 45 minutes each time at room temperature while stirring (followed by filtering and re-suspending solids in fresh methanol after each activation), (iii) activating the resulting solids in N,N-Dimethylacetamide (DMAc) (without LiCl) overnight at room temperature with stirring (followed by filtration of solids), (iv) stirring the resulting solids in 8% by weight LiCl in DMAc for 24 hours at room temperature, followed by (v) performing the same LiCl/DMAc treatment (without any filtration) at 2-8° C. for up to 3 days without stirring. The steps can be performed at ambient pressure. GPC can be performed on cellulose particles treated in this manner after diluting the final solution of particles from 8% LiCl in DMAc to 0.8% LiCl in DMAc.

c. Particle Size

The particles comprising cellulose can have a wide variety of particle sizes. In some aspects, the cellulose particles have a mean particle size of from about 0.1 to about 100 microns. In a further aspect, the cellulose particles have a mean particle size of from about 0.1 to about 90 microns. In a further aspect, the cellulose particles have a mean particle size of from about 0.1 to about 80 microns. In a still further aspect, the cellulose particles have a mean particle size of from about 0.1 to about 70 microns. In yet a further aspect, the cellulose particles have a mean particle size of from about 0.1 to about 50 microns, e.g., from about 0.1 to about 40 microns, from about 0.1 to about 30 microns, from about 0.1 to about 20 microns, from about 0.1 to about 10 microns, from about 0.1 to about 5 microns, from about 0.1 to about 3 microns, from about 0.1 to about 2 microns, or from about 0.1 to about 1.5 microns.

The cellulose particles can also be characterized in terms of particle size distribution, reported as a "$d_n$" value, where "n" represents the percentage of particles in the sample with a diameter less than the $d_n$ value. For example, the $d_{10}$ particle size value indicates that 10% of the sample has a diameter less than the $d_{10}$ value. The $d_{50}$ particle size value (also known as the median diameter) indicates that 50% of the sample has a diameter less than (and more than) the $d_{50}$ value. The $d_{90}$ particle size value indicates that 90% of the sample has a diameter less than the $d_{90}$ value.

In some aspects, the cellulose particles can have a $d_{10}$ of from about 0.1 to about 10 microns, e.g., from about 0.1 to about 8 microns, from about 0.1 to about 5 microns, from about 0.1 to about 3 microns, from about 0.1 to about 1 microns, or from about 0.1 to about 0.6 microns. In further aspects, the cellulose particles can have a $d_{50}$ of from about 0.1 to about 10 microns, e.g., from about 0.1 to about 8 microns, from about 0.1 to about 5 microns, from about 0.1 to about 3 microns, from about 0.1 to about 1 microns, or from about 0.1 to about 0.9 microns. In still further aspects, the cellulose particles can have a $d_{90}$ of from about 0.1 to about 10 microns, e.g., from about 0.1 to about 8 microns, from about 0.1 to about 5 microns, from about 0.1 to about 3 microns, or from about 0.1 to about 1.7 microns.

According to one aspect, the particles can have a $d_{75}$ of less than about 8 microns and/or a $d_{50}$ of from about 0.5 to about 5 microns. Thus, for example, the particles can have a $d_{75}$ of less than about 5 microns and/or a $d_{50}$ of from about 0.5 to about 2 microns, or a $d_{75}$ of less than about 2 microns and/or a $d_{50}$ of from about 0.5 microns to about 1 microns.

In a further aspect, the cellulose particles have particle size distribution characteristics as shown in one of the "Diameter (μm)" of Table 1.

TABLE 1

| PSD Metric | Diameter (μm) | Diameter (μm) | Diameter (μm) | Diameter (μm) | Diameter (μm) | Diameter (μm) |
|---|---|---|---|---|---|---|
| $d_{10}$ | 1.5-7 | 0.1-10 | 0.1-5 | 0.1-2.5 | 0.1-1 | about 0.5 |
| $d_{25}$ | 4-18 | 0.1-14 | 0.1-7 | 0.1-3.5 | 0.1-1.4 | about 0.7 |
| $d_{50}$ | 11-46 | 0.2-18 | 0.2-9 | 0.2-4.5 | 0.2-1.8 | about 0.9 |
| $d_{75}$ | 20-85 | 0.2-22 | 0.2-11 | 0.2-5.5 | 0.2-2.2 | about 1.1 |
| $d_{90}$ | 25-120 | 0.3-30 | 0.3-15 | 0.3-7.5 | 0.3-3 | about 1.5 |
| $d_{99}$ | 50-225 | 0.6-64 | 0.6-32 | 0.6-16 | 0.6-6.4 | about 3.2 |
| Mean | 20-100 | 0.2-20 | 0.2-10 | 0.2-5 | 0.2-2 | about 1 |
| Median | 20-100 | 0.2-18 | 0.2-9 | 0.2-4.5 | 0.2-1.8 | about 0.9 |

Particle sizes can be measured and reported using a Beckman Coulter LS 13 320 Laser Diffraction Particle Size Analyzer instrument with a Universal Liquid Module attached. One of ordinary skill in the art would understand how to prepare samples for particle size analysis with the Beckman Coulter Particle Sizer. While the Beckman Coulter Particle Sizer can be preferred for measuring particle size, if such an instrument is not available, a different instrument known to one of ordinary skill in the art to have comparable measurement results can be employed. Samples for analysis can be prepared in a manner that enables the particles to be analyzed with the instrument. The following sample preparation is illustrative: ensure the solids suspension in the sample is homogeneous in nature before injection into the instrument and, if not homogenous, blend the suspension for ten minutes in a Waring Laboratory Variable Speed Blender before injection into the instrument. The standard software accompanying the Beckman Coulter Particle Sizer provides instructions for use of the instrument and sample preparation.

d. Particle Shape

The cellulose particles can have a variety of shapes, as characterized by transmission electron microscopy (TEM) or scanning electron microscopy (SEM) according to methods known in the art. In some aspects, the cellulose particles have an aspect ratio of from about 1 to about 1.5, e.g., about 1, 1.1, 1.2, 1.3, 1.4, or 1.5. In a further aspect, the particles have a non-spherical shape., e.g., irregular, globular, and the like. In a still further aspect, the particles have a non-spherical shape that is not needle-like or rectangular.

Thus, in some aspects, the particles comprising cellulose comprise at least some type-II cellulose, have a particle size or particle size distribution characteristic shown in one of the "Diameter (μm)" columns of Table 1, an aspect ratio of from about 1 to about 1.5, and a non-spherical shape. In a further aspect, the particles comprising cellulose comprise at least some type-II cellulose and lignin, have a particle size or particle size distribution characteristic shown in one of the "Diameter (μm)" columns of Table 1, an aspect ratio of from about 1 to about 1.5, and a non-spherical shape.

The cellulose particles can also have any composition or characteristic described in U.S. Patent Publication No. 2019/0008749, titled "Manufacture, Isolation, Purification, and Uses of Small Particle Size Cellulose Particles and Compositions," which is incorporated herein by reference in its entirety. In some aspects, the cellulose particles are contained in a slurry product named CELLTICE™ WM (available from Renmatix).

e. Methods of Making the Cellulose Particles

The particles comprising cellulose can be prepared from the hydrolysis of organic material (e.g., wood chips, agricultural residues), biomass, and other cellulose-containing materials, including processes utilizing near critical and supercritical fluids such as supercritical water. The cellulose particles can be isolated from the mixture resulting from the hydrolysis reaction by centrifugation, cyclone separation (including hydrocyclone separation), sedimentation, elutriation, aggregation, flocculation, screening, flotation and skimming, and the like. The feedstock can be any cellulose-containing feed material, such as MCC, nanocrystalline cellulose (NCC), cotton, wood pulp, dissolved wood pulp, or other biomass.

When the particles are prepared from the hydrolysis of biomass, the process can be performed as a one-step or two-step process. In some aspects, the two-step process comprises first processing hydrolysable hemicellulose under mild conditions followed by hydrolyzing cellulose in a second step under more harsh conditions. One advantage of the two-step approach is that the hydrolysis products of hemicellulose can be processed and isolated separately to avoid those products from over-reacting with degradation products resulting from the harsher conditions used to hydrolyze cellulose.

In some aspects, the biomass or cellulose-containing feedstock can be subjected to subcritical, near critical, or supercritical hydrolysis. If necessary or desirable, the biomass or cellulose-containing feedstock can be subjected to size-reduction prior to hydrolysis, e.g., to reduce the average particle size to less than about 500 microns. The size reduction of the feedstock, if desired, can be achieved by an explosive decompression, such as steam explosion, or by comminution, ball-milling or other known techniques. In some aspects, the size reduction step can comprise exploding the cellulose-containing feedstock in the presence of ammonia or sulfur dioxide. When explosive decompression is used, the feedstock is typically in the form of chips (e.g., having a size of ¼ inch, ½ inch, or ⅞ inch). The chips can be hydrolyzed (e.g., auto hydrolyzed) to remove the hemicellulose, and then the resulting chips can be subjected to an explosive decompression process to size-reduce the chips for subsequent near or supercritical hydrolysis to hydrolyze the cellulosic portion. When using a one-step process employing explosive decompression, the chips can be subjected to explosive decompression without prior hydrolysis, and the size-reduced feedstock can be subjected to near or supercritical hydrolysis.

In some aspects, when a hydrolysis process such as supercritical hydrolysis is used to prepare the cellulose particles, the process can involve the use of a fluid at an elevated temperature and/or pressure to convert at least a portion of the type-I cellulose in the feedstock to type-II cellulose and can also be used to hydrolyze at least a portion of the cellulose in the feedstock. In some aspects, the solids content of the mixture subjected to hydrolysis, based on the total weight of the mixture, can be about 1% by weight or more, e.g., up to 40% of higher. In a further aspect, the solids content of the mixture subjected to hydrolysis can be from about 10% by weight to about 30% by weight.

The fluid used for the hydrolysis process can be water, carbon dioxide, sulfur dioxide, methanol, ethanol, isopropanol, propanol, butanol, pentanol, or a combination thereof In some aspects, the fluid comprises, consists of, or consists essentially of water. In a further aspect, the fluid can be a combination of water and ethanol, water and carbon dioxide, or water and sulfur dioxide. In some aspects, the fluid can be in a subcritical state, near critical state, or supercritical state prior to contacting the feedstock. In one aspect, the fluid comprises hot compressed water or supercritical water. In a further aspect, the fluid can be substantially free of an exogenous acid, e.g., an acid is not deliberately added to the fluid. The feedstock stream can be brought into physical contact with the fluid. In some aspects, the feedstock stream and the fluid can form a mixture that, when exposed to hydrolysis conditions (e.g., subcritical, near critical, or supercritical conditions), can generate a fluid stream.

The feedstock mixed with the fluid can be subjected to hydrolysis at a temperature of from about 100 ° C. to about 600 ° C. for a duration sufficient to dissolve at least a portion of feedstock cellulose. Hydrolysis can be carried out under a pressure (in bar) generally up to about 800, or a pressure sufficient to induce a subcritical, near critical, or supercritical state. Hydrolysis can proceed for a sufficient amount of time, e.g., up to about 5 minutes. Hydrolysis can be quenched by reducing the temperature, pressure, or both.

In some aspects, when the hydrolysis product comprises lignin, at least a portion of the lignin can be separated from the cellulose particles, for example through screening, gravity separation, centrifugal separation, centripetal separation, or filtration. In a further aspect, at least a portion of the lignin can be separated from the cellulose particles using a hydrocyclone. The lignin can be removed in an underflow or overflow of the hydrocyclone.

Additional details for preparing the cellulose particles are described in U.S. Patent Publication No. 2019/0008749, titled "Manufacture, Isolation, Purification, and Uses of Small Particle Size Cellulose Particles and Compositions," which is incorporated herein by reference in its entirety.

C. PRODUCTS COMPRISING THE DISPERSIONS

Also disclosed is a dispersion prepared by the disclosed method. According to one aspect, the dispersion can be integrated into a variety of products, particularly aqueous cleansing systems. Non-limiting examples include a hair care product such as shampoo, body wash, personal care or beauty products, cosmetic products, skin care products, other hair care products, lotions, creams, serums, ointments, conditioners, hairsprays, hair gels, deodorants, facial washes, facial or body scrubs, exfoliants, moisturizers, liquid soaps, foundation make-up, bb cream, cc cream, eye cream, sunscreen, anti-acne serum or cream or lotion, cellular serum or cream or lotion, facial or body mask, blush, eyeshadow, mascara, clay or kaolin or mud suspension, hand cream or lotion, face cream or lotion, body cream or lotion, lipstick, or lip balm.

Additionally, the dispersions can be incorporated into pet care products, industrial and home detergents and cleansers, floor cleaners and polishers, e.g., a polisher or cleanser for wood flooring, cleansers for polished, painted, or finished goods such as furniture, architectural trim (e.g., baseboards, columns, chair rails, wainscoting, banisters, paneling, and the like, as well as cleansers for vehicles and machinery such as cars, boats, trucks, trailers, equipment, and the like.

D. EXAMPLES

The following examples are put forth so as to provide those of ordinary skill in the art with a complete disclosure and description of how the methods and products claimed herein are made and evaluated, and are intended to be purely exemplary and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. The Examples are provided herein to illustrate the invention, and should not be construed as limiting the invention in any way.

For the following Examples, CELLTICE™ WM comprised 25% by weight cellulose particles, 20% by weight glycerin, 0.3% by weight glycerin sodium benzoate, 0.2% by weight potassium sorbate, and the balance water. The cellulose particles contained in CELLTICE™ WM have particle size distribution (PSD) characteristics as shown in Table 2.

TABLE 2

| PSD Metric | N | Lower 95% Mean ($\mu$m) | Mean ($\mu$m) | Upper 95% Mean ($\mu$m) | Std. Dev. | Std. Err. Mean |
|---|---|---|---|---|---|---|
| $d_{10}$ | 99 | 0.5338 | 0.5485 | 0.5631 | 0.0733 | 0.0074 |
| $d_{25}$ | 99 | 0.6669 | 0.6765 | 0.6861 | 0.0482 | 0.0048 |
| $d_{50}$ | 99 | 0.8613 | 0.8746 | 0.8878 | 0.0664 | 0.0067 |
| $d_{75}$ | 99 | 1.1268 | 1.1606 | 1.1943 | 0.1692 | 0.0170 |
| $d_{90}$ | 99 | 1.5184 | 1.5956 | 1.6728 | 0.3869 | 0.0389 |
| $d_{99}$ | 99 | 3.2063 | 4.0986 | 4.9910 | 4.4742 | 0.4497 |
| Mean | 99 | 0.9942 | 1.0333 | 1.0725 | 0.1964 | 0.0197 |
| Median | 99 | 0.8545 | 0.8697 | 0.8849 | 0.0762 | 0.0077 |

Compositional details for the concentrate, aqueous phase, and dispersion for Examples 1-5 are provided in Table 3.

TABLE 3

| Compositional Aspect | KL5-23/1 | KL5-30/1 | KL4-95/1 | KL4-95/4 | KL5-33/1 |
|---|---|---|---|---|---|
| Wt. % Hydrophobic Substance(s) in Concentrate* | 50.00 | 50.00 | 50.00 | 50.00 | 50.00 |
| Wt. % Cellulose Particles in Concentrate* | 6.25 | 6.25 | 6.25 | 6.25 | 6.25 |

TABLE 3-continued

| Compositional Aspect | KL5-23/1 | KL5-30/1 | KL4-95/1 | KL4-95/4 | KL5-33/1 |
|---|---|---|---|---|---|
| Hydrophobic Substance(s):Cellulose Particles in Concentrate* | 8:1 | 8:1 | 8:1 | 8:1 | 8:1 |
| Wt. % Water solubles in Concentrate* | 43.75 | 43.75 | 43.75 | 30.00 | 43.75 |
| Hydrophobic Substance(s):Water in the Concentrate* | 1:1.142 | 1:1.142 | 1:1.142 | 1:1.142 | 1:1.142 |
| Wt. % Hydrophobic Substance(s) in Dispersion* | 10.00 | 10.00 | 10.00 | 10.00 | 10.00 |

*prior to mixing with aqueous phase

1. Example 1: Shampoo

Three comparative examples were prepared. KL5-23/1 is a dispersion prepared in which the concentrate was mixed with the aqueous phase after the concentrate and aqueous phase had been separately prepared. KL5-23/2 was prepared according to the same method except without the cellulose particles. KL5-23/3 was prepared using a one-pot approach, wherein the cellulose particles were introduced in the aqueous phase and blended, without first preparing the concentrate separately.

KL5-23/1 resulted in an oil-containing surfactant rich cleanser that is both visually homogenous and stable. Preparing the same composition as two discrete phases but omitting the cellulose particles was demonstrated by KL5-23/2, where the components did not come together in a homogenous fashion and manifested as a discrete oil layer atop the water phase. Using a one-pot approach, as with KL5-23/3, the result was discretely separated phases indicative of the surfactant eliminating the emulsification potential of the oil phase and yielding an end product akin to having no cellulose particles at all, similar to KL5-23/2.

To evaluate the foaming characteristics of the three comparative examples, a small quantity of the dispersion was introduced into an excess of water in a graduated cylinder and inverted 10 times. The initial height of the foam was noted and monitored over the course of 60 minutes to assess relative changes, plotted in FIG. 1. In KL5-23/2, there was an abundance of free surfactant to create foam initially, as there were no cellulose particles present to interfere. However, the weight and presence of the oil depletes the foam (relatively) over the course of 60 minutes. The preferred composition KL5-23/1 created less initial foam, but the stability was significantly higher as denoted by the reduced slope shown in FIG. 1. For KL5-23/1, the oil droplets were more adequately dispersed, and the surfactant regulated the size of the droplets to restrict the impact on foam stability. In the final example, KL5-23/3, the one-pot approach failed to yield a significant foam like KL5-23/2, and the result was unstable. A shampoo was prepared from KL5/23-1. The shampoo lathered well in hair. After washing, the hair felt clean and not greasy.

Compositional details for the three comparative examples (KL5-23/1, KL5-23/2, and KL5-23/3) is provided in Table 4.

TABLE 4

| Item | Ingredient | KL5-23/1 | KL5-23/2 | KL5-23/3 |
|---|---|---|---|---|
| | Aqueous Phase | | | |
| 1 | Deionized Water | 41.50% | 46.50% | 41.50% |
| 2 | Acrylate Copolymer | 6.00% | 6.00% | 6.00% |
| 3* | Sodium Cocoyl Isethionate | 10.00% | 10.00% | 10.00% |
| 4* | Sodium Lauroyl Methyl Isethionate | 10.00% | 10.00% | 10.00% |
| 5* | Cocamidopropyl Betaine | 8.00% | 8.00% | 8.00% |
| 6* | Cocamide MEA | 2.00% | 2.00% | 2.00% |
| 7 | Panthenol | 1.00% | 1.00% | 1.00% |
| 8 | Potassium Hydroxide | 0.50% | 0.50% | 0.50% |
| | Hydrophobic Phase | | | |
| 9† | *Simmondsia Chinesis* (Jojoba) Seed Oil | 8.80% | 8.80% | 8.80% |
| 10† | *Helianthus Annuus* (Sunflower) Seed Oil (and) *Amaranthus Caudatus* Seed Extract (and) Diisostearyl Malate (and) *Rosmarinus Officinalis* (Rosemary) Leaf Extract | 1.00% | 1.00% | 1.00% |
| 11† | Borage Oil | 0.10% | 0.10% | 0.10% |
| 12† | Evening Primrose Oil | 0.10% | 0.10% | 0.10% |
| 13 | CELLTICE ™ WM (Renmatix) | 5.00% | — | 5.00% |
| 14 | Deionized Water | 5.00% | 5.00% | 5.00% |
| 15 | Diocide | 1.00% | 1.00% | 1.00% |

*Surfactants
†Hydrophobic Substances

2. Example 2: Shampoo

A shampoo was prepared from a dispersion as described in Table 5.

TABLE 5

| | | Ingredient | KL5- |
|---|---|---|---|
| Item | Trade Name | INCI Name | 30/1 |
| | | Aqueous Phase | |
| 1 | Deionized Water | Water | 30.80% |
| 2 | METHOCEL ™ 40-0101 PCG (Dow) | Hydroxypropyl Methylcellulose | 0.50% |
| 3 | CARBOPOL ™ Aqua SF-1 Polymer (Lubrizol) | Acrylates Copolymer | 8.00% |

TABLE 5-continued

| Item | Trade Name | INCI Name | KL5-30/1 |
|---|---|---|---|
| 4* | NANSA ™ LSS 38/U (Innospec) | Sodium C14-16 Olefin Sulfonate | 20.00% |
| 5* | ISELUX ™ LQ-CLR-SB (Innospec) | Sodium Lauroyl Methyl Isethionate | 10.00% |
| 6* | CHEMBETAINE ™ CGF (Lubrizol) | Cocamidopropyl Betaine | 8.00% |
| 7 | Ritapan D (Rita) | Panthenol | 1.00% |
| 8 | Potassium Hydroxide (Various Suppliers) | Potassium Hydroxide | 0.50% |
| | | Hydrophobic Phase | |
| 9† | Jojoba Oil (Various Suppliers) | *Simmondsia Chinensis* (Jojoba) Seed Oil | 8.80% |
| 10† | AMA Oil (Centerchem) | *Helianthus Annuus* (Sunflower) Seed Oil (and) *Amaranthus Caudatus* Seed Extract (and) Diisostearyl Malate (and) *Rosmarinus Officinalis* (Rosemary) Leaf Extract | 1.00% |
| 11† | Borage Oil (Various Suppliers) | *Borago Officinalis* Seed Oil | 0.10% |
| 12† | Evening Primrose Oil (Various Suppliers) | *Oenothera Biennis* (Evening Primrose) Oil | 0.10% |
| 13 | CELLTICE ™ WM (Renmatix) | Cellulose Particle Slurry (25 wt % Cellulose Particles) | 5.00% |
| 14 | Deionized Water | Water | 5.00% |
| 15 | Citric Acid (Various Suppliers) | Citric Acid | 0.20% |
| 16 | DIOCIDE ™ (Centerchem) | Caprylyl Glycol (and) Phenoxyethanol (and) Hexylene Glycol | 1.00% |

*Surfactants
†Hydrophobic Substances

In a main vessel, water was weighed. Ritapan D was dissolved in the water, followed by the addition of CAR-BOPOL Aqua SF-1. Methocel 40-101 was sprinkled in with rapid mixing until uniform. CHEMBETAINE CGF was then added and mixed until uniform. Potassium hydroxide was added and mixed until uniform. The mixture thickened and become more clear. The mixing speed was reduced, followed by the addition of Iselux LQ-CLR and NANSA LSS 38 AV, which were mixed until fully dissolved. In a separate vessel, CELLTICE was added along with deionized water, followed by the hydrophobic substances (oils). The concentrate was stirred at room temperature into the aqueous phase with paddle or propeller mixing. Citric acid and DIOCIDE were then added. The pH of the dispersion was 6.3, viscosity was 32,806 cps, as determined on a Brookfield LVDVII+ TF @ 6 rpm for 1 min with Helipath on.

3. Example 3: Body Wash

A body wash was prepared from a dispersion as described in Table 6.

TABLE 6

| Item | Trade Name | INCI Name | KL4-95/1 |
|---|---|---|---|
| | | Aqueous Phase | |
| 1 | Deionized Water | Water | 45.32% |
| 2 | VERSENE ™ 220 (Dow Chemical) | Tetrasodium EDTA | 0.1% |
| 3* | Pureact I-85EC (Innospec) | Sodium Cocoyl Isethionate | 10.00% |
| 4* | CHEMBETAINE ™ CGF (Lubrizol) | Cocamidopropyl Betaine | 10.00% |
| 5* | Protamid CME (Protameen Chemicals) | Cocamide MEA | 2.00% |
| 6 | D-Panthenol (Various Suppliers) | Panthenol | 1.00% |
| 7 | BIOWAX ™ 754 Special (Biosil Technologies, Inc.) | PEG-8 Dimethicone | 1.00% |
| 8 | CARBOPOL ™ Aqua SF-1 Polymer (Lubrizol) | Acrylates Copolymer | 8.00% |
| 9 | Potassium Hydroxide (Various Suppliers) | Potassium Hydroxide | 0.50% |
| 10 | Resveratrol BT (Bio Component Research) | Water (and) Polygonum Cuspidatum Root Extract (and) Phenoxyethanol (and) Sodium Benzoate | 1.00% |

TABLE 6-continued

| | Ingredient | | KL4- |
|---|---|---|---|
| Item | Trade Name | INCI Name | 95/1 |
| 11 | White Tea BT (Bio Component Research) | Water (and) Camellia Sinensis Leaf Extract (and) Phenoxyethanol | 1.00% |
| 12 | KATHON ™ CG (Dow Chemical) | Methylchloroisothiazolinone (and) Methylisothiazolinone | 0.08% |
| | | Hydrophobic Phase | |
| 13† | Jojoba Oil (Various Suppliers) | *Simmondsia Chinensis* (Jojoba) Seed Oil | 10.00% |
| 14 | CELLTICE ™ WM (Renmatix) | Cellulose Particle Slurry (25 wt % Cellulose Particles) | 5.00% |
| 15 | Deionized Water | Water | 5.00% |

*Surfactants
†Hydrophobic Substances

A vessel was charged with deionized water, and VERESENE 220 was added and dissolved therein. The vessel was heated to about 80° C. Vigorous mixing was reduced and Pureact I-85, CHEMBETAIN CGF and Protamid CME were added, followed by mixing until uniform. The mixture was cooled to 40° C. while mixing. CARBOPOL Aqua SF-1 was added, followed by potassium hydroxide, followed by mixing until uniform. The pre-blended concentrate comprising the hydrophobic substances was then added and homogenized with the aqueous phase.

4. Example 4: Body Wash

A body wash was prepared from a dispersion as described in Table 7.

TABLE 7

| | Ingredient | | KL4- |
|---|---|---|---|
| Item | Trade Name | INCI Name | 95/4 |
| | | Aqueous Phase | |
| 1 | Deionized Water | Water | 40.30% |
| 2* | Ritafactant 138 ANEC (Rita Corp.) | Decyl Glycoside (and) Sodium Lauroyl Lactylate (and) Disodium Coco-glucoside Citrate | 20.00% |
| 3* | Cocomidopropyl Betaine (Various Suppliers) | Cocomidopropyl Betaine | 10.00% |
| 4 | D-Panthenol (Various Suppliers) | Panthenol | 1.00% |
| 5 | CARBOPOL ™ Aqua SF-1 Polymer (Lubrizol) | Acrylates Copolymer | 5.00% |
| 6 | Potassium Hydroxide (Various Suppliers) | Potassium Hydroxide | 0.50% |
| 7 | Resveratrol BT (Bio Component Research) | Water (and) Polygonum Cuspidatum Root Extract (and) Phenoxyethanol (and) Sodium Benzoate | 1.00% |
| 8 | White Tea BT (Bio Component Research) | Water (and) Camellia Sinensis Leaf Extract (and) Phenoxyethanol | 1.00% |
| 9 | Citric Acid (Various Suppliers) | Citric Acid | 0.20% |
| 10 | Diocide (Centerchem) | Caprylyl Glycol (and) Phenoxyethanol (and) Hexylene Glycol | 1.00% |
| | | Hydrophobic Phase | |
| 11† | Jojoba Oil (Various Suppliers) | *Simmondsia Chinensis* (Jojoba) Seed Oil | 10.00% |
| 12 | CELLTICE ™ WM (Renmatix) | Cellulose Particle Slurry (25 wt % Cellulose Particles) | 5.00% |
| 13 | Deionized Water | Water | 5.00% |

*Surfactants
†Hydrophobic Substances

Deionized water was added to a main vessel, and pan-thenol was dissolved therein. Ritafactant d138 ANEC, coco-midopropyl betaine, and CARBOPOL Aqua SF-1 were added and mixed until uniform. Potassium hydroxide was added and mixed until uniform. Resveratrol BT, BC BT White Tea, and Diocide were then added. The pre-blended concentrate comprising the hydrophobic substances was then added and homogenized with the aqueous phase.

5. Example 5: Body Wash

A body wash was prepared from a dispersion as described in Table 8.

5.9, with a viscosity of 42,803 cPa, as determined on a Brookfield LVDVII+ TF @ 6 rpm for 1 min. with Helipath on.

6. Example 6: Foam Stability

Foam stability was tested for three formulations: (/1)—body wash and water; (/2)—body wash, water, and jojoba oil; and (/3) — body wash, water, jojoba oil and CELL-TICE™ WM (Renmatix). For each formulation, a 10% shampoo solution was prepared. Drainage values were (/1)—14%; (/2)—31%, and (/3)—24%. The compositions of each formulation are shown below in Table 9.

TABLE 8

| Item | Trade Name | INCI Name | KL5-33/1 |
|---|---|---|---|
| | | Aqeuous Phase | |
| 1 | Deionized Water | Water | 36.70% |
| 2 | VERSENE ™ 220 (Dow Chemical) | Tetrasodium EDTA | 0.1% |
| 3* | Sulfochem ES-2PK (Lubrizol) | Sodium Laureth Sulfate | 20.00% |
| 4* | CHEMBETAINE ™ CGF (Lubrizol) | Cocamidopropyl Betaine | 10.00% |
| 5 | D-Panthenol (Various Suppliers) | Panthenol | 1.00% |
| 6 | Methocel 40-0101 PCG (Dow) | Hydroxypropyl Methylcellulose | 0.50% |
| 7 | CARBOPOL ™ Aqua SF-1 Polymer (Lubrizol) | Acrylates Copolymer | 8.00% |
| 8 | Potassium Hydroxide (Various Suppliers) | Potassium Hydroxide | 0.50% |
| 9 | Resveratrol BT (Bio Component Research) | Water (and) Polygonum Cuspidatum Root Extract (and) Phenoxyethanol (and) Sodium Benzoate | 1.00% |
| 10 | White Tea BT (Bio Component Research) | Water (and) Camellia Sinensis Leaf Extract (and) Phenoxyethanol | 1.00% |
| 11 | Citric Acid (Various Suppliers) | Citric Acid | 0.20% |
| 12 | Diocide (Centerchem) | Caprylyl Glycol (and) Phenoxyethanol (and) Hexylene Glycol | 1.00% |
| | | Hydrophobic Phase | |
| 13† | Jojoba Oil (Various Suppliers) | *Simmondsia Chinensis* (Jojoba) Seed Oil | 10.00% |
| 14 | CELLTICE ™ WM (Renmatix) | Cellulose Particle Slurry (25 wt % Cellulose Particles) | 5.00% |
| 15 | Deionized Water | Water | 5.00% |

*Surfactants
†Hydrophobic Substances

Deionized water was added to a main vessel. VERSENE 220 was added an dissolved therein. Methocel 40-101 was dispersed in the resulting mixture. CARBOPOL Aqua SF-1 and CHEMBETAINE CGF and mixed until uniform. Potas-sium hydroxide was added and mixed until uniform, fol-lowed by Sulfochem ES-2 PK. Resveratrol BT, White Tea, citric acid, and DIOCIDE were added and mixed until uniform. The pre-blended concentrate comprising the hydro-phobic substances was then added to the aqueous phase and homogenized until uniform. The pH of the dispersion was

TABLE 9

| Item | (/1) %(w/w/) | (/2) % (w/w/) | (/3) %(w/w/) |
|---|---|---|---|
| Irish Spring Body Wash Gel Douche | 80.00 | 80.00 | 80.00 |
| Deionized Water | 20.00 | 10.00 | 0 |
| Jojoba Oil | 0 | 10.00 | 0 |
| Jojoba Oil Dispersion* | | | 20.00 |

*5 parts deionized water, 5 parts CELLTICE WM, 5 parts Jojoba oil

The formulations were diluted to 10% as shown in Table 10.

TABLE 10

| Weight | (/1) (g) | (/2) (g) | (/3) (g |
|---|---|---|---|
| Shampoo | 20.1 | 20.1 | 20.0 |
| Shampoo + Deionized Water | 200.0 | 200.2 | 200 |

Four grams of the shampoo solution were added to 146 grams of water (50 ppm harness) at 29° C. The solution was agitated for 10 seconds at a medium speed in a blender. The foam was then poured into a 1,000 mL graduated cylinder and the volume was measured. After 3.5 minutes, the position of the foam in the water interface was recorded (drainage).

The volume of foam at time zero and after 3.5 minutes is shown in Table 11. The shampoo (/1) produced the highest amount of foam, 390 ml. The foam decreased by 15% after 3.5 minutes. The shampoo (/2) produced 74% of the foam that (/1) produced and its volume was reduced by 31% in 3.5 minutes. The addition of CELLTICE WM, sample (/3), improved the foam creation and reduced the foam drainage over sample (/2). Sample (/3) produced 90% of the foam that (/1) produced and it was reduced by 24% after 3.5 minutes. The terms foam decrease, and zero foam capacity were calculated according to equations 1 and 2 respectively. The results show that incorporation of the cellulose particles into the system reduces the amount of foam drainage.

TABLE 11

| | Volume | | |
|---|---|---|---|
| | (/1) (mL) | (/2) (mL) | (/3) (mL) |
| Time zero, total | 440 | 340 | 375 |
| Time zero, water | 50 | 50 | 25 |
| Time zero, foam | 390 | 290 | 350 |
| 3.5 mins., total | 440 | 325 | 375 |
| 3.5 mins., water | 110 | 125 | 110 |
| 3.5 mins., foam | 330 | 200 | 265 |
| Foam Decrease in 3.5 mins. ($FD_{3.5}$) | 15% | 31% | 24% |
| Zero Foam Capacity ($FC_0$) | 100% | 74% | 90% |

Equation 1:

$$FD_{3.5} = \frac{\text{Foam Volume}_0 - \text{Foam Volume}_{3.5}}{\text{Foam Volume}_0} * 100\%$$

Equation 2:

$$FC_0 = \frac{\text{Foam Volume ``}n\text{''}_0}{\text{Foam Volume ``}/1\text{''}_0} * 100\%$$

7. Example 6: Sulfate-Free Hand Wash

Three sulfate-free hand washes with nourishing natural oils were prepared according to the formulations shown in Table 12.

TABLE 12

| Item | Ingredient Trade Name | INCI Name | KL5-30/3 | KL5-30/4 | KL5-30/5 |
|---|---|---|---|---|---|
| | | Aqueous Phase | | | |
| 1 | Deionized Water | Water | 30.10% | 30.10% | 30.10% |
| 2 | Methocel 40-0101 PCG (Dow) | Hydroxypropyl Methylcellulose | 0.50% | N/A | N/A |
| 3 | JAGUAR ™ Excel (Solvay) | Guar Hydroxypropyltrimonium Chloride | N/A | 0.50% | 0.50% |
| 4 | CARBOPOL ™ Aqua SF-1 Polymer (Lubrizol) | Acrylates Copolymer | 8.00% | 8.00% | 8.00% |
| 5* | NANSA ™ LSS 38/U (Innospec) | Sodium C14-16 Olefin Sulfonate | 20.00% | 20.00% | 20.00% |
| 6* | ISELUX ™ LQ-CLR-SB (Innospec) | Sodium Lauroyl Methyl Isethionate | 10.00% | 10.00% | 10.00% |
| 7* | CHEMBETAINE ™ CGF (Lubrizol) | Cocamidopropyl Betaine | 8.00% | 8.00% | 8.00% |
| 8 | Ritapan D (Rita) | Panthenol | 1.00% | 1.00% | 1.00% |
| 9 | Potassium Hydroxide | Potassium Hydroxide | 0.50% | 0.50% | 0.50% |
| 10 | Citric Acid (Various Suppliers) | Citric Acid | 0.20% | 0.20% | 0.20% |
| 11 | SPECTRASTAT ™ GN2 (Inolex) | Caprylhydroxamic Acid, Glyceryl Caprylate, Glycerin | 1.20% | 1.20% | 1.20% |
| | | Hydrophobic Phase | | | |
| 12 | Jojoba Oil (Various Suppliers) | *Simmondsia Chinensis* (Jojoba) Seed Oil | 8.80% | 9.80% | 9.80% |
| 13† | AMA Oil (Centerchem) | *Helianthus Annuus* (Sunflower) Seed Oil (and) *Amaranthus Caudatus* Seed Extract (and) Diisostearyl Malate (and) *Rosmarinus Officinalis* (Rosemary) Leaf Extract | 1.00% | N/A | N/A |
| 14† | Borage Oil (Various Suppliers) | *Borago Officinalis* Seed Oil | 0.10% | 0.10% | 0.10% |
| 15† | Evening Primrose Oil (Various Suppliers) | *Oenothera Biennis* (Evening Primrose) Oil | 0.10% | 0.10% | 0.10% |
| 16 | CELLTICE ™ WM (Renmatix) | Cellulose Particle Slurry (25 wt % Cellulose Particles) | 5.00% | 5.00% | N/A |
| 17 | Cellulose 100-micron Slurry | | N/A | N/A | 5.00% |

TABLE 12-continued

| Item | Ingredient Trade Name | INCI Name | KL5-30/3 | KL5-30/4 | KL5-30/5 |
|------|-----------------------|-----------|----------|----------|----------|
| 18 | Deionized Water | Deionized Water | 5.00% | 5.00% | 5.00% |
| 19 | Orchidia ORC 1800971 EO Subtle | | 0.50% | 0.50% | 0.50% |

*Surfactants
†Hydrophobic Substances

Ingredient 17 (cellulose 100-micron slurry) comprised 25% by weight cellulose particles and 75% by weight water. The cellulose particles had the following compositional characteristics: 88.8% cellulose, 4.6% hemicellulose, 5.3% lignin, 0.2% ash. The particles in the slurry had the following particle size distribution characteristics: 3.4 micron ($d_{10}$), 8.7 micron ($d_{25}$), 22.9 micron ($d_{50}$), 41.2 micron ($d_{75}$), 59.1 micron ($d_{90}$), and 112.1 micron ($d_{99}$).

KL5-30/3 was prepared according to a method analogous to that described in Example 2. KL5-30/4 and KL5-30/5 were prepared as follows: Deionized water was added to a main vessel, JAGUAR Excel was added with rapid mixing until fully dispersed. The dispersion was heated to 70° C., followed by slow mixing. ISELUX and CHEMBETAINE were added and mixed until uniform. CARBOPOL was added and mixed until uniform. NANSA was added and mixed until uniform. Potassium hydroxide was added with rapid mixing while taking care not to aerate. The resulting mixture was cooled to 40° C. and citric acid and SPEC-TRASTAT GN2 were added. The mixture was cooled to 30° C. or lower. In a separate vessel, deionized water and either CELLTICE WM (KL5-30/4) or cellulose 100-micron slurry (KL5-30/5) was added and mixed until coarsely dispersed. Jojoba, Borage, and Evening Primrose Oils were added to the dispersion, which was then homogenized. The dispersion was added to the aqueous phase, Orchida was added as a fragrance, and the resultant dispersion was mixed until uniform.

It will be apparent to those skilled in the art that various modifications and variations can be made without departing from the scope or spirit of this disclosure. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method for making a dispersion, the method comprising:
(a) preparing an aqueous phase comprising water and a surfactant in an amount of from 30 to 40 wt % based on the total weight of the aqueous phase, wherein the surfactant is a sulfate, sulfonate, isethionate, carboxylate, sarcosinate, amino acid-based surfactant, non-ionic surfactant, soap, sulfoacetate, or a combination thereof;
(b) preparing a hydrophobic phase at ambient temperature, wherein the hydrophobic phase comprises: comprising
(i) a hydrophobic substance in an amount of from 40 to 60 wt % based on the total weight of the hydrophobic phase,
(ii) water in an amount of from 20 to 50 wt % based on the total weight of the hydrophobic phase, and (iii) a plurality of particles comprising cellulose in an amount of from 20 to 30 wt % based on the total weight of the hydrophobic phase,
wherein the hydrophobic substance comprises an oil, a silicone, a fat, an emollient, a triester of glycerol, or a combination thereof, and
wherein the particles have:
(i) a mean particle size of from about 0.1 to about 100 microns;
(ii) an aspect ratio of from about 1 to about 1.5; and
(iii) a non-spherical shape,
wherein at least a portion of the cellulose is type-II cellulose, thereby providing a concentrate; and
(c)-mixing the aqueous phase and the concentrate at ambient temperature, thereby providing the dispersion.
2. The method of claim 1, wherein the particles comprise lignin.
3. The method of claim 2, wherein the weight % of lignin in the particles is from about 1 to about 30.
4. The method of claim 1, wherein the particles have a crystallinity determined by x-ray diffraction (XRD) of 60% or more.
5. The method of claim 1, wherein the particles have a d75 of less than 25microns and/or a d50 of from about 0.5 microns to 20 microns.
6. The method of claim 1, wherein the aqueous phase, the concentrate, and the dispersion are substantially free of volatile organic solvent.
7. The method of claim 1, wherein the concentrate is not contacted with a surfactant prior to step (c).
8. The method of claim 1, wherein the surfactant has a hydrophile-lipophile balance (HLB) number of greater than 10.
9. The method of claim 1, wherein the hydrophobic substance is synthetic or derived from a plant or other organic matter.
10. The method of claim 1, wherein the hydrophobic substance and the plurality of particles are combined with a preservative during step (b).
11. The method of claim 1, wherein the weight % of the hydrophobic substance in the dispersion is at least 10.
12. The method of claim 1, wherein the dispersion is a homogeneous dispersion.
13. The method of claim 1, wherein the dispersion is a stable emulsion.
14. A method for making a dispersion, the method comprising:
(a) preparing an aqueous phase comprising water and a surfactant, wherein the surfactant is a sulfate, sulfonate, isethionate, carboxylate, sarcosinate, amino acid-based surfactant, non-ionic surfactant, soap, sulfoacetate, or a combination thereof,
wherein the ratio of the surfactant to the water in the aqueous phase ranges from 0.7 to 1.5;
(b) preparing a hydrophobic phase at ambient temperature, wherein the hydrophobic phase comprises comprising a hydrophobic substance, water, and a plurality of particles comprising lignin and cellulose, at least a portion of which is type-II cellulose, wherein the hydrophobic substance comprises an oil, a silicone, a fat, an emollient, a triester of glycerol, or a combination thereof, and wherein the particles have:

(i) a mean particle size of from about 0.1 to about 100 microns;

(ii) an aspect ratio of from about 1 to about 1.5; and (iii) a non-spherical shape, thereby providing a concentrate; and (d) mixing the aqueous phase and the concentrate at ambient temperature, thereby providing the dispersion, wherein the weight % of the hydrophobic substance in the concentrate prior to step (c) is from about 40 to about 60;

wherein the ratio of the hydrophobic substance to the plurality of particles in the concentrate prior to step (c) is from about 10:1 to about 2:1 about 6:1;

wherein the ratio of the hydrophobic substance to the water in the concentrate prior to step (c) is from about 1:1 to about 2:1, wherein the weight % of water in the concentrate prior to step (c) is from about 20 to about 50; and wherein the weight % of particles in the concentrate prior to step (c) is from about 0.05 to about 30.

15. A dispersion prepared by the method of claim 1, the method comprising:

(a) preparing an aqueous phase comprising water and a surfactant in an amount of from 30 to 40 wt % based on the total weight of the aqueous phase, wherein the surfactant is a sulfate, sulfonate, isethionate, carboxylate, sarcosinate, amino acid-based surfactant, non-ionic surfactant, soap, sulfoacetate, or a combination thereof, (b) preparing a hydrophobic phase at ambient temperature, wherein the hydrophobic phase comprises:

(i) hydrophobic substance in an amount of from 40 to 60 wt % based on the total weight of the hydrophobic phase, (ii) water in an amount of from 20 to 50 wt % based on the total weight of the hydrophobic phase, and (iii) a plurality of particles comprising cellulose in an amount of from 20 to 30 wt % based on the total weight of the hydrophobic phase, wherein the hydrophobic substance comprises an oil, a silicone, a fat, an emollient, a triester of glycerol, or a combination thereof, and wherein the particles have:

(i) a mean particle size of from about 0.1 to about 100 microns;

(ii) an aspect ratio of from about 1 to about 1.5; and ii) a non-spherical shape, wherein at least a portion of the cellulose is type-II cellulose, thereby providing a concentrate; and (c) mixing the aqueous phase and the concentrate at ambient temperature, thereby providing the dispersion.

16. A powder, grain, paste, concentrate, or foam comprising the dispersion of claim 15.

17. A cleaning product comprising the dispersion of claim 15.

18. A personal or beauty product comprising the dispersion of claim 15.

* * * * *